(12) United States Patent
Kafrawy

(10) Patent No.: US 6,497,994 B1
(45) Date of Patent: Dec. 24, 2002

(54) PHOTOLITHOGRAPHIC PROCESS FOR THE FORMATION OF A ONE-PIECE NEEDLE

(75) Inventor: Adel Kafrawy, Kingston, MA (US)

(73) Assignee: Ethicon, Inc., Somerville, NJ (US)

( * ) Notice: Subject to any disclaimer, the term of this patent is extended or adjusted under 35 U.S.C. 154(b) by 14 days.

(21) Appl. No.: 09/608,672

(22) Filed: Jun. 29, 2000

(51) Int. Cl.[7] .................................................. G03F 7/00
(52) U.S. Cl. .......................... 430/320; 430/323; 163/5; 606/223
(58) Field of Search ................................. 430/320, 323; 163/1.5; 606/167, 222, 223

(56) References Cited

U.S. PATENT DOCUMENTS

| | | | |
|---|---|---|---|
| 4,587,202 A | 5/1986 | Borysko | 430/320 |
| 4,777,096 A | 10/1988 | Borysko | 428/571 |
| 5,057,401 A | 10/1991 | Borysko et al. | 430/320 |
| 5,676,008 A | * 10/1997 | Morin | 72/129 |
| 5,730,741 A | * 3/1998 | Horzewski | 606/1 |
| 5,762,811 A | 6/1998 | Munoz | 216/11 |

* cited by examiner

Primary Examiner—Kathleen Duda
(74) Attorney, Agent, or Firm—Blakely, Sokoloff, Taylor & Zafman, LLP

(57) ABSTRACT

A method and an apparatus is disclosed for forming a one-piece introducer needle having a member portion and a needle portion by introducing a photoresist on a substrate. The temperature of the substrate is increased and then decreased. A photomask is deposited onto a substrate.

17 Claims, 26 Drawing Sheets

One-piece Needle Inserted into One-piece Catheter and Hub

PHOTOLITHOGRAPHIC PROCESS FOR THE FORMATION OF A ONE-PIECE NEEDLE

BACKGROUND OF THE INVENTION

1. Field of the Invention

This invention relates generally to intravascular assemblies, and more specifically to a one-piece introducer needle and method of making the needle.

2. Background

Intravascular devices such as catheter assemblies are generally used for passing fluids between a device such as a syringe or a drip to or from body lumens such as veins or arteries, or other internal target sites. Such an assembly usually includes a hub, and a catheter tube. The tube is typically secured to the hub by means of an eyelet ring that is press fit within the nose of the hub. This hub and tube assembly is then mounted over an introducer needle comprising a sharp needle attached to a plastic hub. The sharp tip of the needle, protruding from the catheter tip, is used for piercing a body lumen so that access may be gained into the body lumen by the needle and subsequently the catheter. Once the catheter and the needle are located within the body lumen, the introducer needle is removed and discarded while the catheter tube remains in the body lumen. A syringe or a tube of a drip is then attached to the hub so that fluids may be passed through the hub and the catheter from the drip or the syringe to the body lumen. The hub is typically made of materials that provide sufficient rigidity thereto and the catheter tube is usually made of a material which is flexible.

Intravenous introducer needles with a surface groove are known in the art. One purpose of intravenous introducer needles is to allow a healthcare worker to be able to quickly observe when back-flow of blood enters a surface groove indicating that the needle has penetrated the vein.

Introducer hollow needles are conventionally made, one at a time, by a multistep process involving considerable time, labor, and precision machinary. For example, stainless steel hollow wire is straightened, cut to the desired length, tapered, and treated with a variety of finishing steps. There are additional disadvantages to introducer needles such as those described in U.S. Pat. No. 5,279,572, issued to Hokam ("Hokam"), and European Patent No. EPO 893 137 A2, issued to Terumo Kabushiki Kaisha. For instance, Hokam comprises an intravenous introducer needle having two blood back-flow passage routes in which the needle comprises a material that is made of steel. The needle and the handle are manufactured separately through a machining operation and thereafter are fastened together. By requiring that a stainless steel needle be joined to a needle base, an assembling cost is incurred. It is therefore desirable to have a method of fabricating a one-piece needle that is able to reduce the operational cost such as machining of the needle and handle, and the cost of assembling these elements.

SUMMARY

A method is disclosed for forming a one-piece introducer needle having a head. The method comprises introducing a photoresist material onto a substrate. The temperature of the substrate is increased and then cooled. A photomask is then deposited onto the substrate. The substrate is then exposed to light. A one-piece needle is formed from this process. Additional features, embodiments, and benefits will be evident in view of the figures and detailed description presented herein.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION

One embodiment of the invention relates to forming a one-piece introducer needle for use in an intravascular assembly by a photolithography process. Photolithography is a process that involves creating in and on the substrate surface dimensions that are close to the design dimensions. Photolithography also involves the correct alignment of the pattern onto the surface of the substrate.

Another embodiment of the invention relates to the formation of a beveled sharp end of the distal tip of the needle. Another embodiment of the invention relates to forming a single piece introducer needle with a groove.

Referring to the figures, exemplary embodiments of the invention will now be described. The exemplary embodiments are provided to illustrate aspects of the invention and should not be construed as limiting the scope of the invention.

Figure 1:
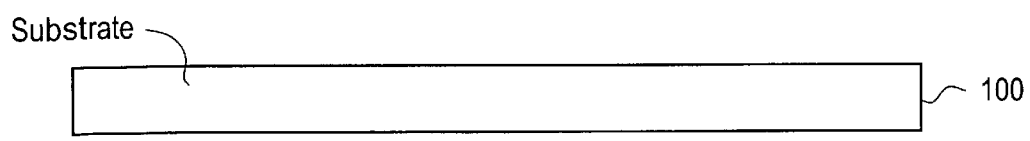
FIG. 1 illustrates a substrate in accordance with one embodiment of the invention.

FIGS. 1–6 illustrate one embodiment of the invention using a method related to photolithography to form a one-piece needle. FIG. 1 illustrates a substrate that may include a metal or other materials such as polymer or ceramic material. If metal is used as a substrate, the metal sheet should have a tensile strength of at least about 300,000 psi, a Rockwell C hardness of at least about 40–45, and ductility so that the needle may not be bent. The metals that may be used include stainless steel such as a stainless steel 410, Gin 5, Gin 6 razorblade grade stainless steel, and molybdenum. The thickness of the steel may be about 0.0250 inches or less.

Figure 2:
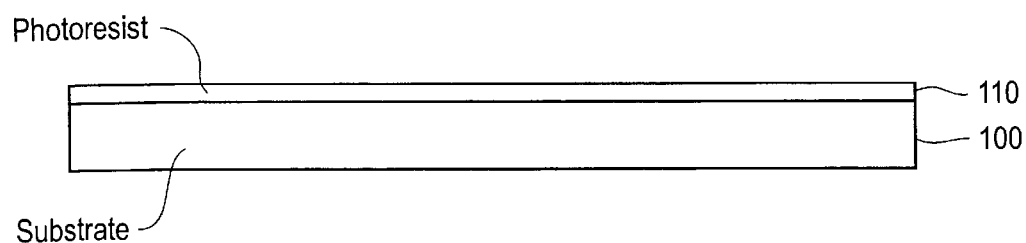
FIG. 2 illustrates the substrate as in FIG. 1, in which a photoresist is introduced onto the substrate in accordance with one embodiment of the invention.

FIG. 2 illustrates photoresist 110 introduced over substrate 100 in accordance with one embodiment of the invention. Photoresist 110 is a light sensitive material. Exposure to light causes changes to its structure and properties. Either a positive-acting photoresist or a negative-acting photoresist may be used. A positive-acting photoresist when exposed to light, changes the chemical structure from a relatively nonsoluble condition to a more soluble condition which is referred to as photosolubilization. A negative-acting photoresist, on the other hand, when exposed to light is changed from a soluble condition to an insoluble condition which is referred to as polymerization. A negative-acting photoresist outlines the portion outside of the one-piece needle that is to be removed. In contrast, a positive-acting photoresist outlines the one-piece needle itself. For purposes of illustration only, a negative photoresist is used to represent photoresist 110.

Figure 7:
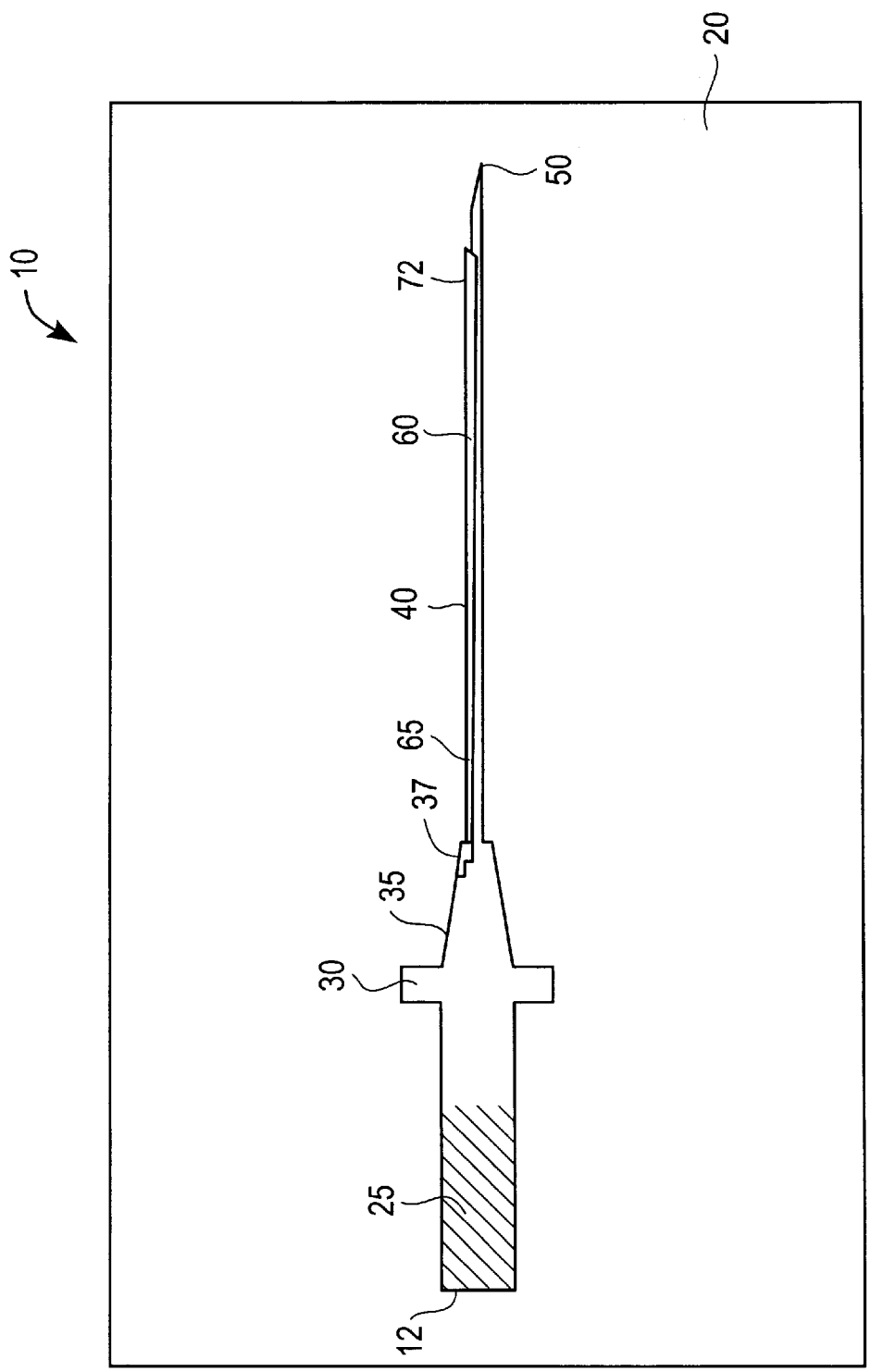
FIG. 7 illustrates a one-piece needle inserted into a catheter and hub in accordance with one embodiment of the invention.

Photoresist 110 may include negative photoresists such as KMER or RISTON that are commercially available from DuPont located in Wilmington, Del. Photoresist 110 and substrate 100 is then baked at a moderately elevated temperature for several minutes such as at about 70° C. to 90° C. for approximately 10 minutes to dry the coating. Other temperatures may be used. The temperature used depends upon the photoresist used and the amount of photoresist applied to substrate 100. After substrate 100 and photoresist 110 have been allowed to cool for a certain amount of time such as about five minutes. A photomask having a negative image of the plurality of the one-piece needles to be fabricated is positioned over the coated top surface of the substrate 100. Substrate 100 and photoresist 110 are then exposed to light in the image of a plurality of one-piece needles as illustrated in FIG. 7. The plurality of one-piece needles include a variety of shapes such as that which is shown in FIGS. 7, 14, 16, 18, 20, 22, or any other suitable shape.

Figure 3:
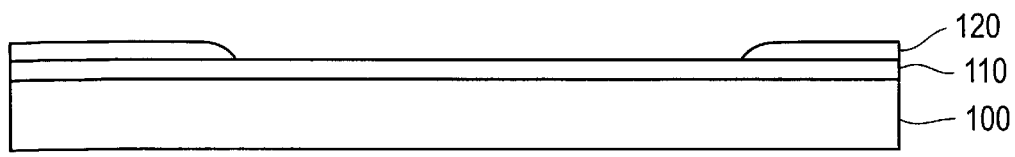
FIG. 3 illustrates the same substrate as in FIG. 2 in which a photomask has been introduced over the photoresist in accordance with one embodiment of the invention.

FIG. 3 illustrates a first photomask 120 introduced over photoresist 110. Photoresist 110 may be deposited over substrate 100 using a variety of methods such as by using a screen over substrate 100 and spraying photoresist 110 over substrate 100 or any other suitable method. First photomask 120 includes suitable commercially available photomasks. First photomask 120 covers photoresist 110 such that an outline of a needle is formed as shown in FIG. 3.

Figure 4:
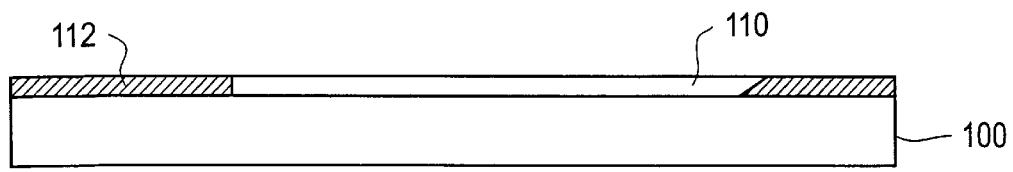
FIG. 4 illustrates the same substrate as in FIG. 3 in which the substrate is exposed to light in accordance with one embodiment of the invention.
Figure 5:
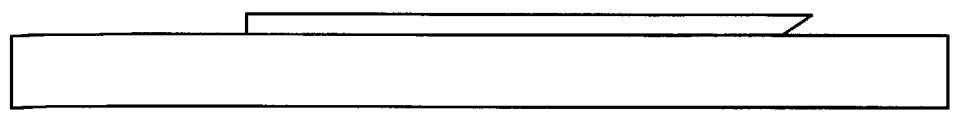
FIG. 5 illustrates a one-piece needle formed after unnecessary material has been removed from the substrate shown in FIG. 4 in accordance with one embodiment of the invention.
Figure 6:
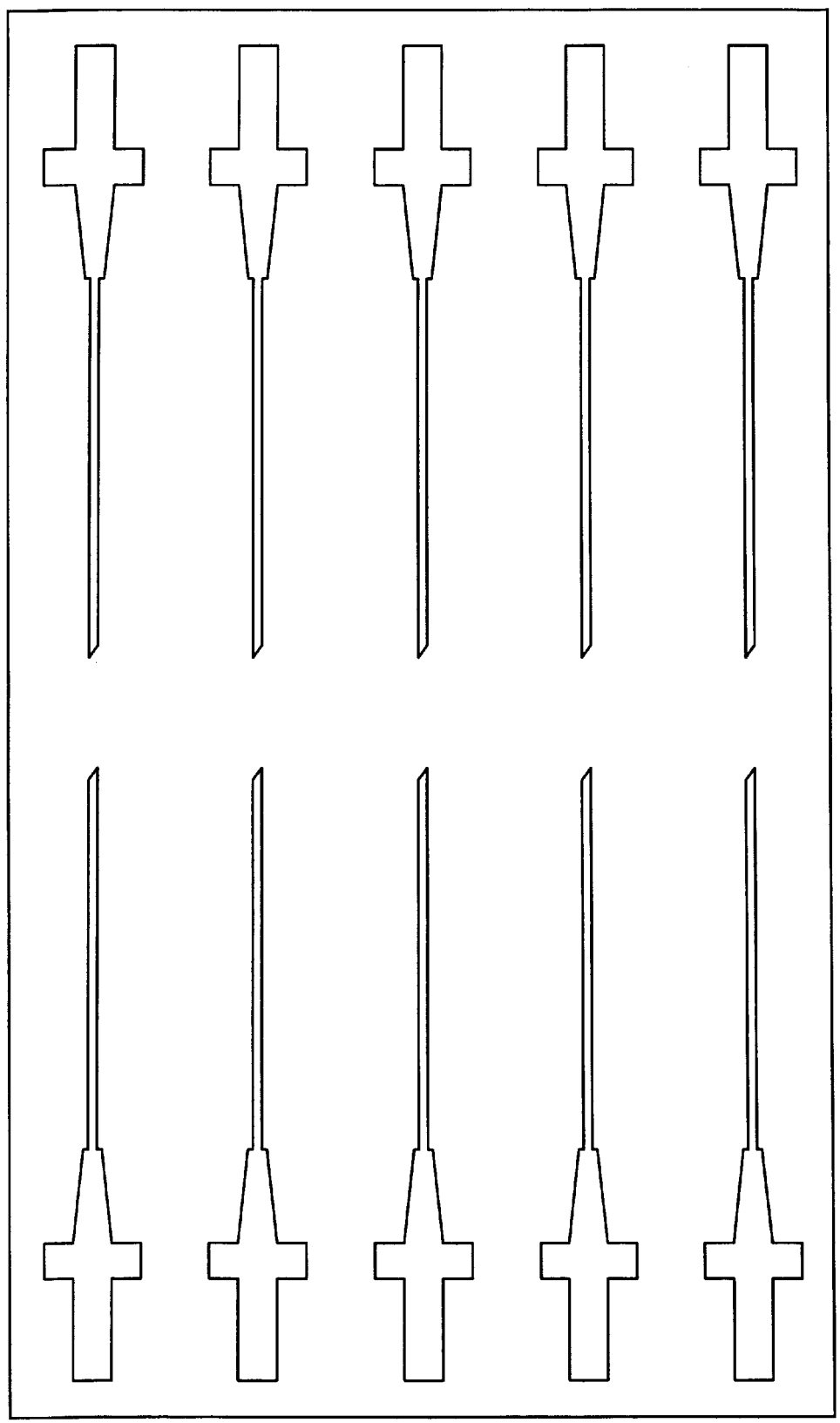
FIG. 6 illustrates a plurality of a one-piece needle in accordance with one embodiment of the invention.

FIG. 4 illustrates substrate 100 having undergone exposure to light. The light source that is used to expose photoresist 110 to light may be ultraviolet radiation, a carbon-arc light, mercury-vapor lamps, ultraviolet rich fluorescent lights or any other suitable light. Substrate 100 is exposed to the light from a couple seconds to several minutes depending upon the nature and the power of the light source, the distance of the light from the photoresist 110, and the sensitivity of the photoresist 110 that is chosen. FIG. 4 illustrates a one-piece needle of a plurality of one-piece needles formed from substrate 100. After exposure to the light, the photoresist 110 is rinsed in a suitable solution such as any one of several commercially available developers to remove the unexposed photoresist 112. Thereafter, FIG. 5 illustrates a single one-piece needle formed from the substrate. FIG. 6 illustrates a plurality of one-piece needles formed from the sheet of metal that was used as a substrate for the formation of a plurality of needles. After rinsing, the sheet of metal with the photoresist 110 in the form of intravenous needles, may be baked at, for example, 120° C. to 260° C. for 3 to 12 minutes to further harden the remaining photoresist 110.

The next operation is to etch away the unnecessary metal in an etching process. The metal may be etched using an etching solution, plasma or any other suitable etching process. Typical etching solutions include 36–40° Baumé aqueous ferric chloride, an aqueous mixture of ferric chloride and hydrochloric acid, or a mixture of aqueous hydrochloric acid and nitric acid, or other suitable material. These etching solutions, etching processes, and the photoetching process are known in the art.

After the etching step, the plurality of one-piece needles are removed from the etching solution. The plurality of needles are then washed and dried. Each needle is separated from the plurality of needles formed. The process described in FIGS. 1–6 is then repeated to form another sheet of one-piece needles. It will be appreciated that the process described in FIGS. 1–6 may be repeated to the other side of substrate 100. This allows for creative designs of one-piece needles such as the one-piece needles shown in FIGS. 14, 16, 18, and 22.

The type of designs of one-piece needles that may be formed from this process is limited only by the creativity of the manufacturer. It will be appreciated that the process described in FIGS. 1–5 are used to form the different designs that are presented below.

FIG. 7 illustrates one-piece needle 10 comprises a head in the shape of a handle 25, a flange 30 portion of the handle, a tapered portion 35 of handle 25, a stepped portion 37 of the handle 25, a needle 40, wherein the needle portion has a surface groove 60, and a beveled portion 55 that transitions to a distal sharp tip 50 of needle 40. Surface groove 60 extends from proximal end 65 of surface groove 60 to the distal end 72 of the groove channel.

The dimensions of the one-piece needle that is formed varies with the gauge of the intravascular assembly to be fabricated. In this embodiment, a solid tip needle with a surface groove is formed. The outer diameter of the handle may range from approximately 0.25 inches to 0.35 inches in the proximal portion of the handle. The inner diameter of the proximal portion of handle 25 may range from approximately 0.20 inches to 0.30 inches. The outer diameter of flange 30 may range from approximately 0.50 inches to 0.80 inches. The inner diameter of flange 30 may range from approximately 0.40 inches to 0.60 inches. Tapered portion of handle 25 has an inner and an outer diameter that varies with the tapered portion of a particular needle being formed. However, the range of outer diameters of the tapered portion may range from 0.20 inches to 0.30 inches. Similarly, the inner diameter of the tapered portion may range approximately from 0.15 inches to 0.25 inches. The first stepped portion of handle 25 has an outer diameter that ranges from approximately 0.30 inches to 0.40 inches and the inner diameter ranges from approximately 0.25 inches to 0.35 inches. Second stepped portion of handle 25 has an outer diameter that ranges from 0.25 inches to 0.35 inches and an inner diameter that ranges from approximately 0.20 inches to 0.30 inches, and a length that ranges from approximately 0.25 inches to 0.75 inches. Needle 40 may have a length that ranges from approximately 0.70 inches to 2.5 inches, an outer diameter that ranges from approximately 0.10 inches to 0.02 inches. It will be appreciated that a solid tip needle lacks the inner diameter dimensions listed for the proximal portion of handle 25, flange 30, the tapered portion of handle 25, the first and second stepped portions of handle 25.

In FIG. 7, needle 40 that is formed has a solid tip but a surface groove is formed therein. Surface groove 60 allows blood to enter needle 40 at or near the distal end of needle 40. The blood moves in the proximal direction of needle 40 as shown in FIG. 7. It will be appreciated that the surface groove channel in FIG. 7 illustrates that since the surface groove channel is formed on the external portion of the needle, there is no outer diameter for the surface groove channel. The distance from proximal end 65 and distal end 72 of surface groove 60 ranges from approximately 0.25 inches to 2.5 inches.

Figure 8:
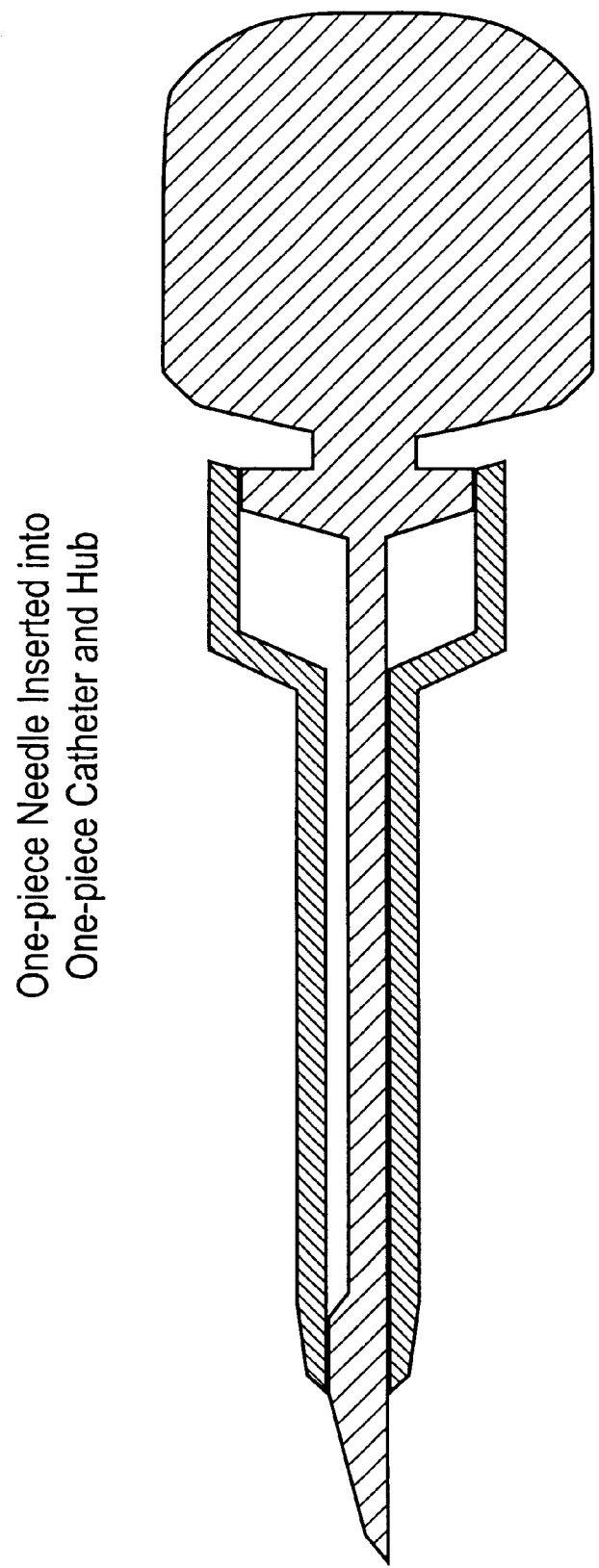
FIG. 8 illustrates a one-piece needle inserted into a catheter and hub in accordance with an embodiment of the invention.

FIG. 8 illustrates the one-piece needle formed from the process shown in FIGS. 1 through 5 inserted into a catheter and hub. It will be appreciated that the one-piece needle tip formed from this process may be either solid or solid with surface groove. The surface groove may have a variety of shapes as illustrated in FIGS. 9 to 13, and 24, to 29.

Figure 9:
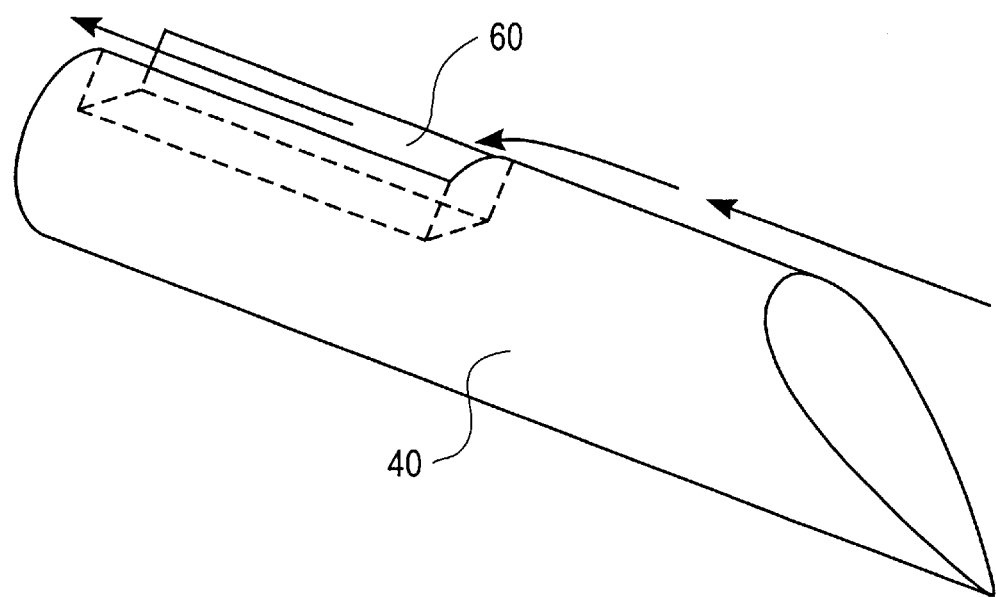
FIG. 9 illustrates an isometric view of blood entering a surface groove of a solid tip-surface grooved needle in accordance with one embodiment of the invention.
Figure 10:
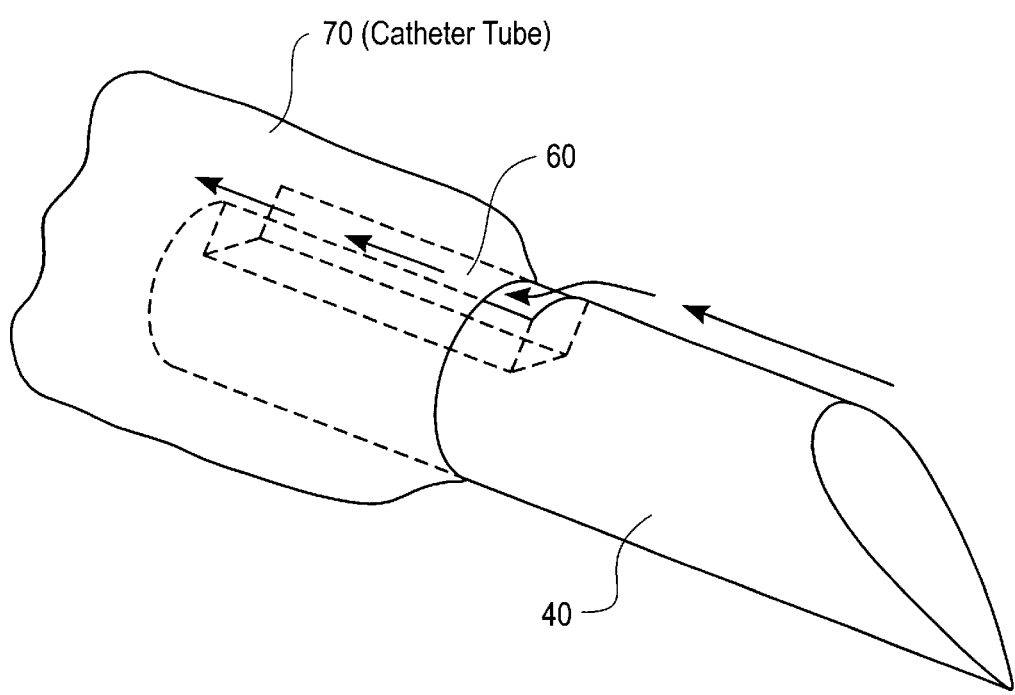
FIG. 10 illustrates an isometric view of blood entering a surface groove of a solid tip-surface grooved needle inserted into a catheter tube in accordance with one embodiment of the invention.
Figure 11:
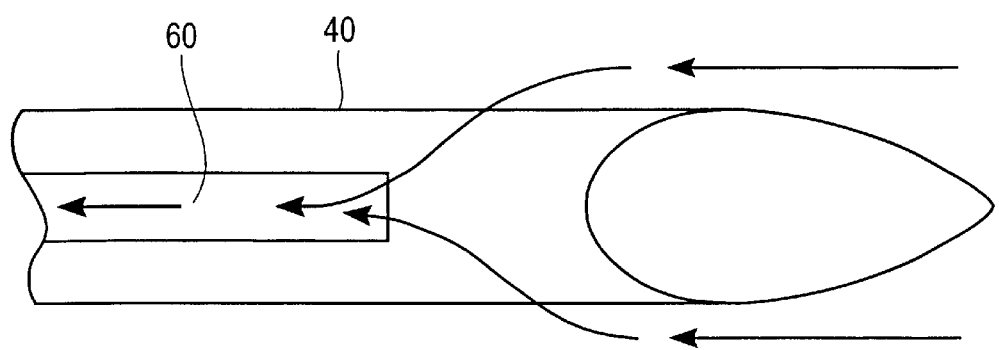
FIG. 11 illustrates a top view of blood entering a surface groove of a solid tip-surface grooved needle in accordance with one embodiment of the invention.

FIGS. 9 through 11 illustrate one embodiment of the invention in which a needle 40 has a solid tip portion and a surface groove 60. FIGS. 9 and 10 provide isometric views of solid needle 40 and shows the flow of blood passing over the distal tip of needle 40 and entering surface groove 60. FIG. 10 further illustrates the flow of blood when needle 40 is coupled to a catheter tube 70. FIG. 11 illustrates a top view of needle 40 wherein blood flows around solid tip needle 40 and enters surface groove 60.

Figure 12:
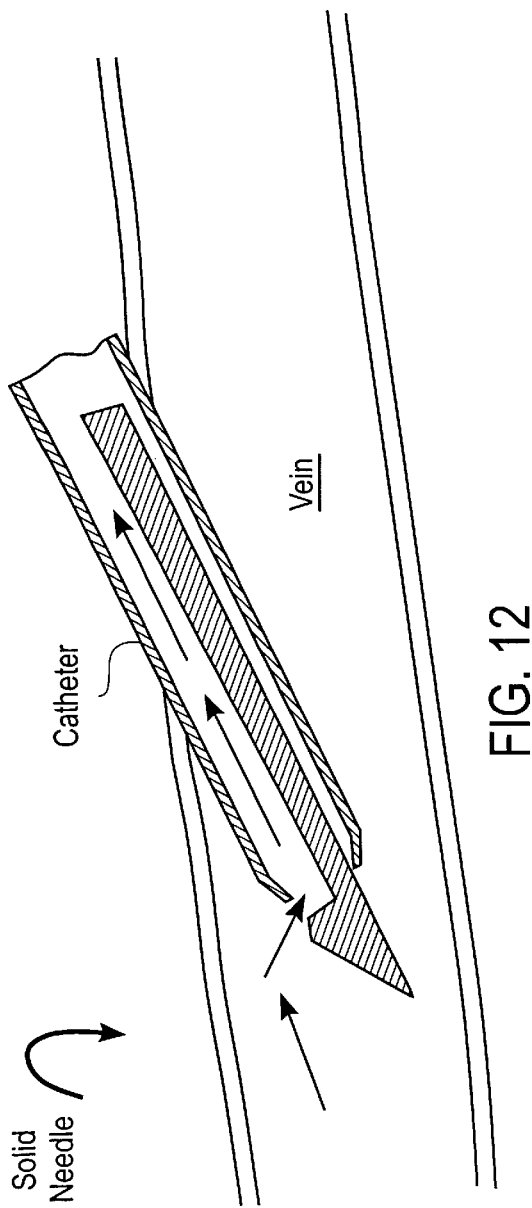
FIG. 12 illustrates an isometric view of blood entering a surface groove of a solid tip needle in accordance with one embodiment of the invention.
Figure 13:
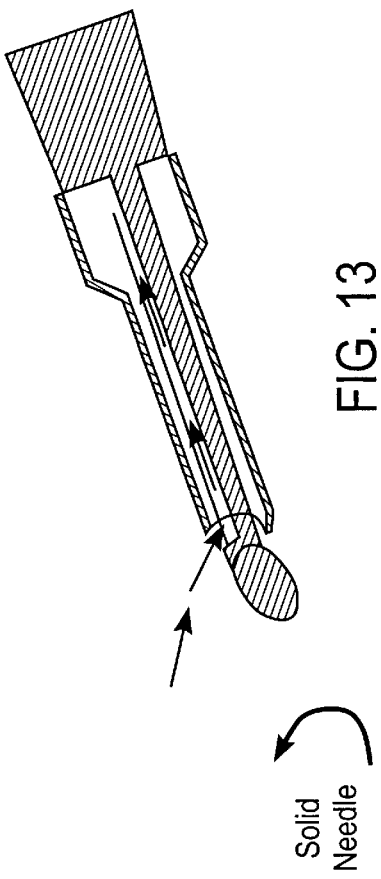
FIG. 13 illustrates a top view of blood entering a surface groove of a solid tip needle in accordance with one embodiment of the invention.

FIGS. 12 and 13 illustrate needle 40 and needle tip with a pointed end inserted into a patient's vein. The needle tip is a solid sharp. The blood flows into the surface groove and travels to the proximal end of needle 40. Given the explanation of a surface groove in the one-piece needle, the following description presents a variety of different shaped one-piece needles such as needles having different shaped heads and one-piece needles with and without surface grooves.

Figure 14:
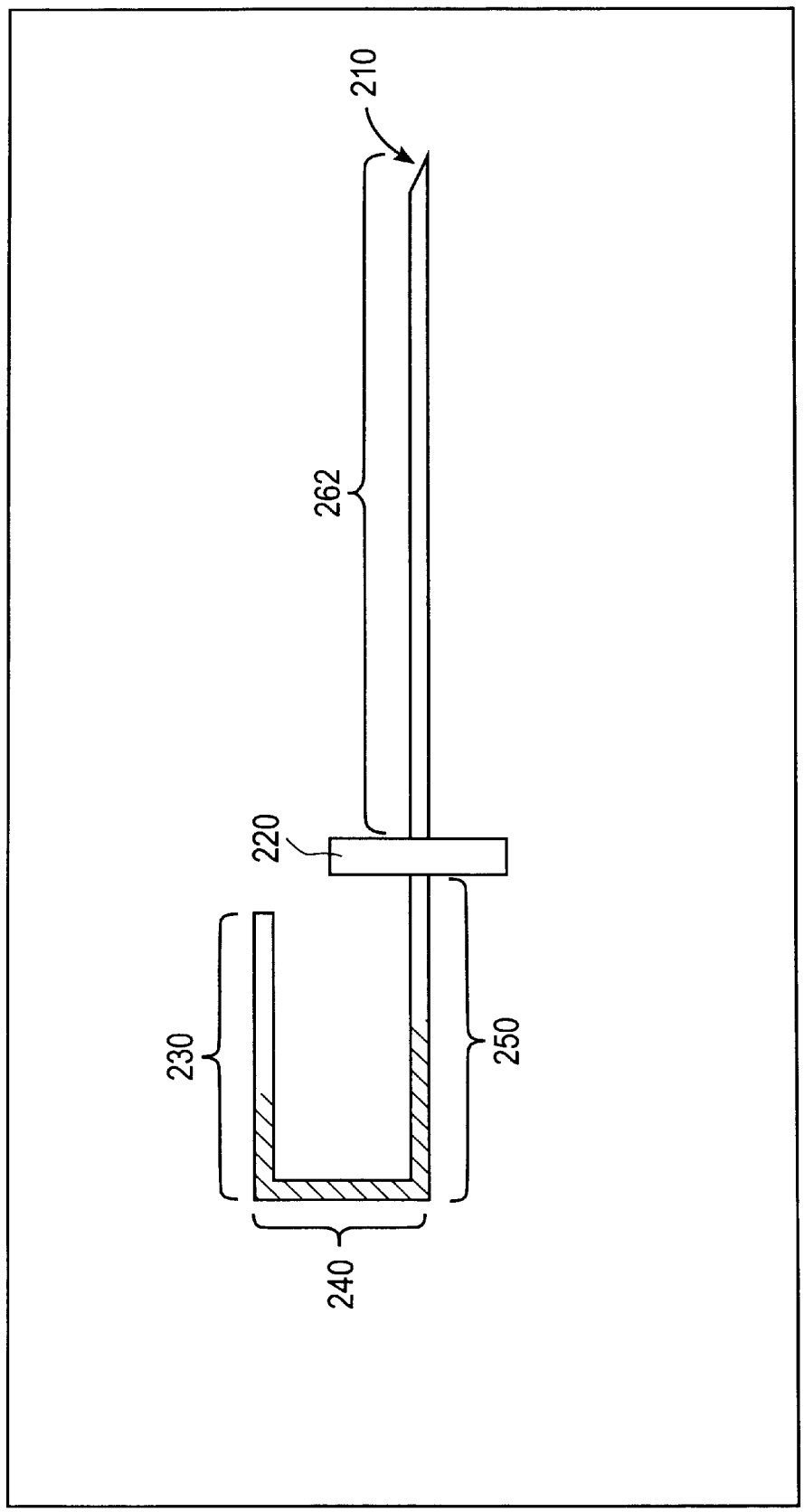
FIG. 14 illustrates a one-piece needle that has a needle head that is substantially rectangular.
Figure 15:
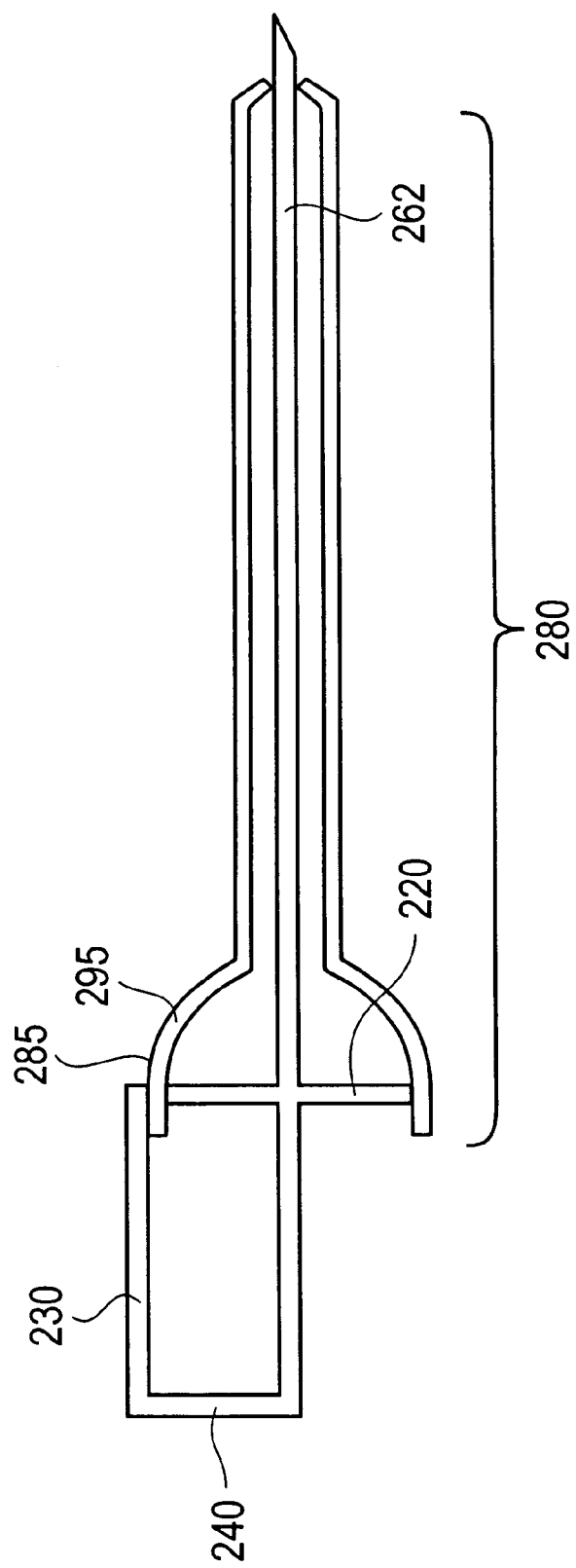
FIG. 15 illustrates a one-piece needle inserted into a catheter and hub in accordance with one embodiment of the invention.

FIG. 14 illustrates one embodiment of the invention for forming a one-piece needle. The one-piece needle comprises a substantially rectangular portion at the proximal end formed by portions 230, 240, and 250. Disk portion 220 is located at the proximal end of the one-piece needle. One purpose of disk portion 220 is locking the one-piece needle into a catheter and hub as illustrated in FIG. 15. The one-piece needle then transitions into a distal portion of one-piece needle 262. The one-piece needle further comprises a beveled distal tip 210 at the distal end of the one-piece needle.

It will be appreciated that the dimension of the one-piece introducer needle that is formed vary with the gauge of the intravascular assembly to be fabricated. For example, the distal portion of one-piece needle 262 may range in length from 0.7 inches to 2.5 inches. Furthermore, disk portion 220 may range in diameter from 0.15 inches to 0.35 inches. This large range is present to accommodate the design of a luer lock feature in the hub. Portion 250 may range from 0.5 inches to 2.0 inches. Portion 240 may range from 0.5 inches to 2.0 inches. Portion 230 may range from 0.5 inches to 2.0 inches. It will be appreciated that the diameter of the needle is the same as that which is described above and is dependent upon the gauge of the intravascular assembly to be fabricated.

FIG. 15 illustrates the one-piece needle formed from the process illustrated in FIGS. 1–5 inserted into a catheter and hub 280. It will be appreciated that the one-piece needle formed from the process illustrated in FIGS. 1–5 is snapped into place at block 285 that has a recessed region for receiving portion 230. It will also be appreciated that disk portion 220 is locked in place at block 285 that also has a recessed region within the inner surface of hub 295. When the one-piece needle snaps into place, a noise is emitted such as a clicking noise. This clicking noise indicates to the healthcare worker that the needle is locked in place. The blood flows from the distal portion of one-piece needle 262 and flows toward disk portion 220. Disk portion 220 prevents the blood from exiting hub 295.

Figure 16:
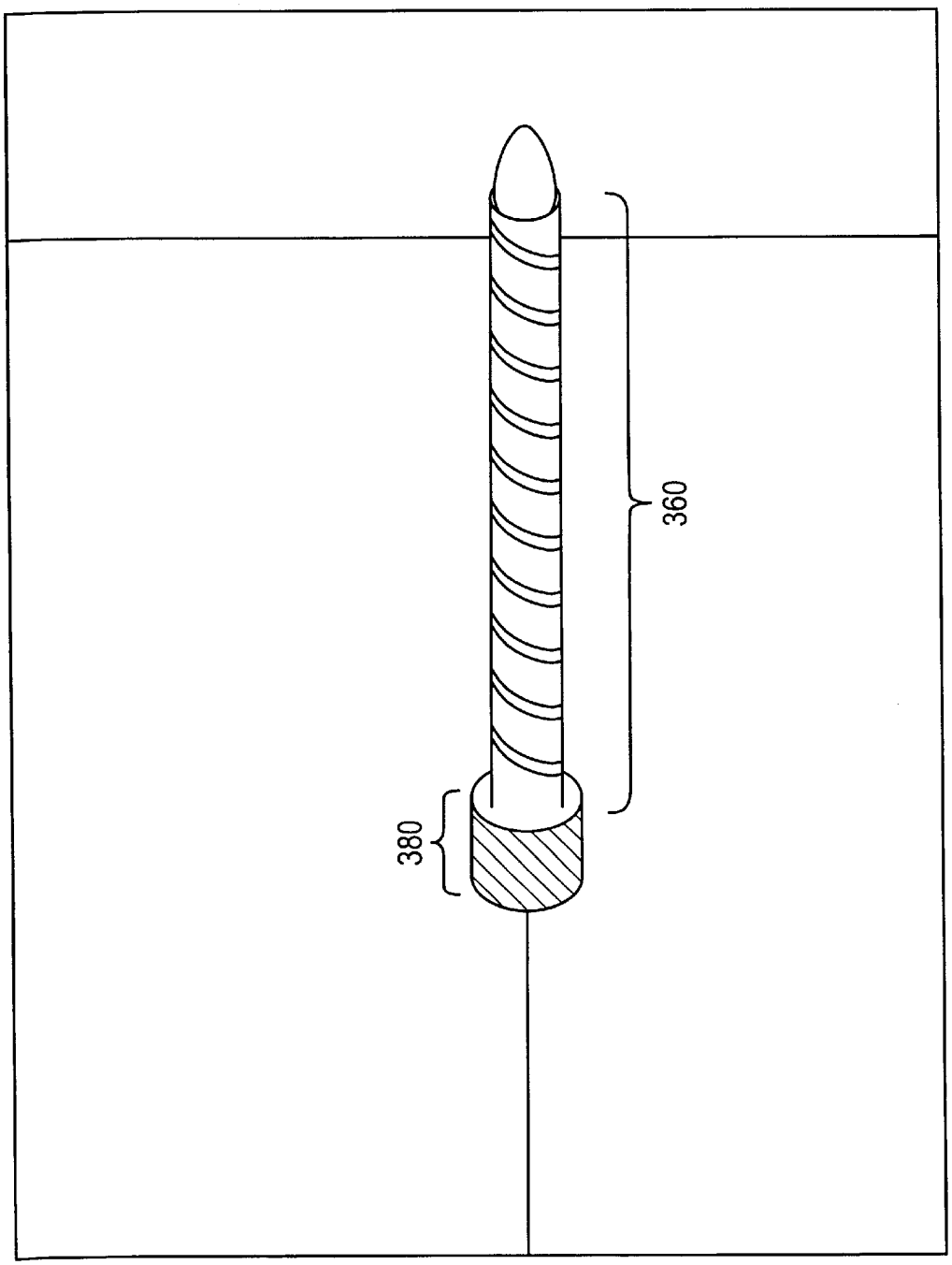
FIG. 16 illustrates a one-piece spiral needle in accordance with one embodiment of the invention.

FIG. 16 illustrates a one-piece spiral needle in accordance with one embodiment of the invention. The one-piece needle formed by photolithography comprises a proximal (or head) portion 380 and the distal portion 360. The distal portion 360 has spirals throughout the length of distal portion 360. In contrast, a proximal portion typically lacks spirals although it will be appreciated that it may have spirals in an alternate embodiment. It will be also be appreciated that the number of spirals depend upon the requirements of the health care worker. For example, the more spirals used, the more blood volume the needle can accommodate. This provides the healthcare worker with a better opportunity to observe flashback. The spirals that are formed extend toward the center of the one-piece needle. The diameter of the recesses may range from 0.03 to 0.2 inches.

In order to form spirals, after one side has completed the photolithographic process, the substrate is flipped and undergoes the process illustrated in FIGS. 1–5. In this manner, a plurality of spirals may be formed. Additionally, the one-piece needle may have a groove portion at the top portion of the one-piece needle. The groove potion is also formed by implementing techniques of the invention.

Figure 17:
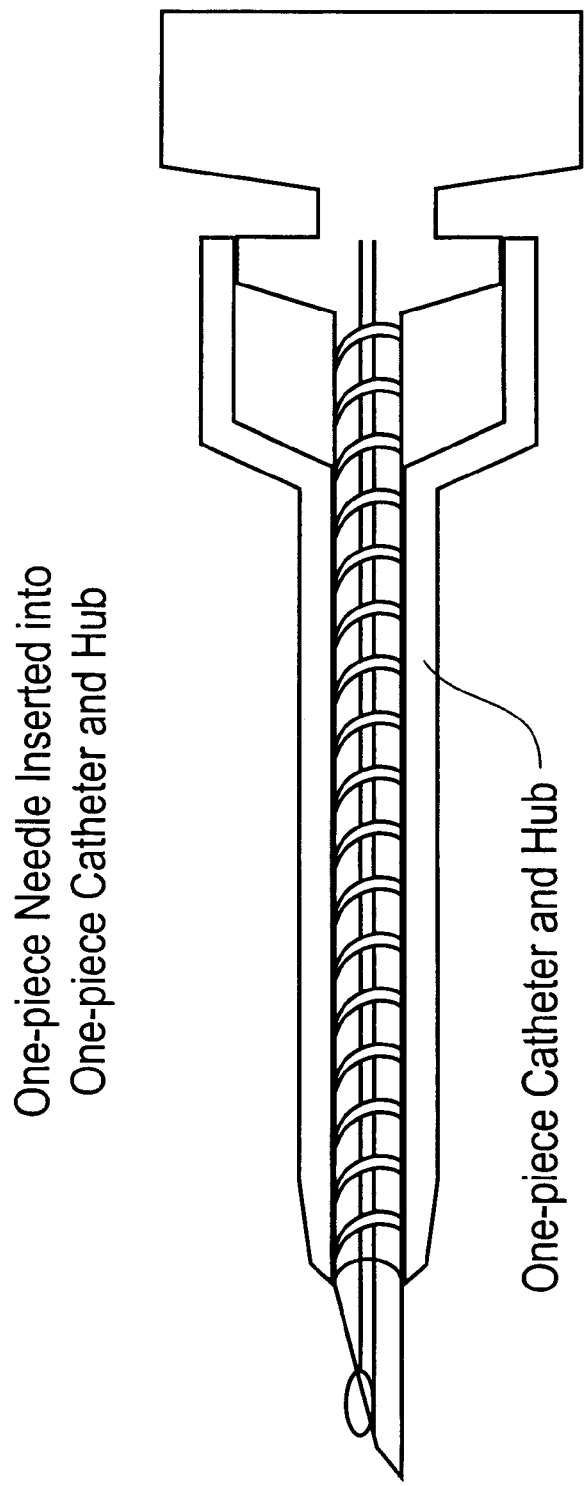
FIG. 17 illustrates the one-piece spiral needle inserted into a catheter and hub in accordance with one embodiment of the invention.

FIG. 17 illustrates the one-piece spiral needle inserted into a catheter and hub. The hub is located at 395. The diameter of the one-piece spiral needle and hub may range from 0.15 inches to 0.35 inches. The number of spirals that may be used for the lowest to the highest gauge may range from 5 to 15.

Figure 18:
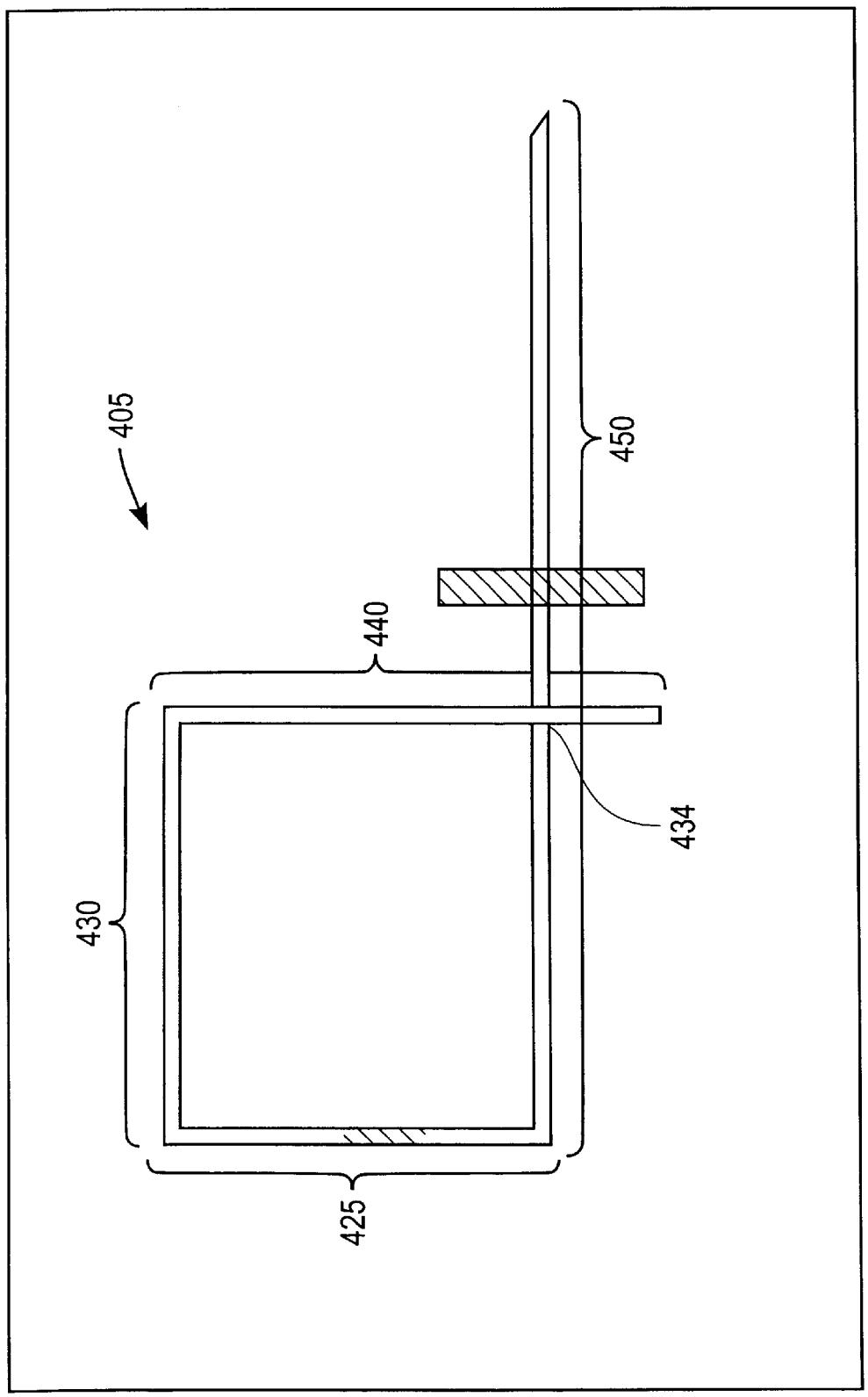
FIG. 18 illustrates a one-piece needle having a substantially rectangular head of in accordance with one embodiment of the invention.

FIG. 18 illustrates one embodiment of the invention for forming a one-piece needle. The one-piece needle comprises a substantially rectangular portion head (or handle) shaped head 425 and a distal portion 450 of the one-piece needle. At point 434, portion 440 does communicate with portion 450.

Figure 19:
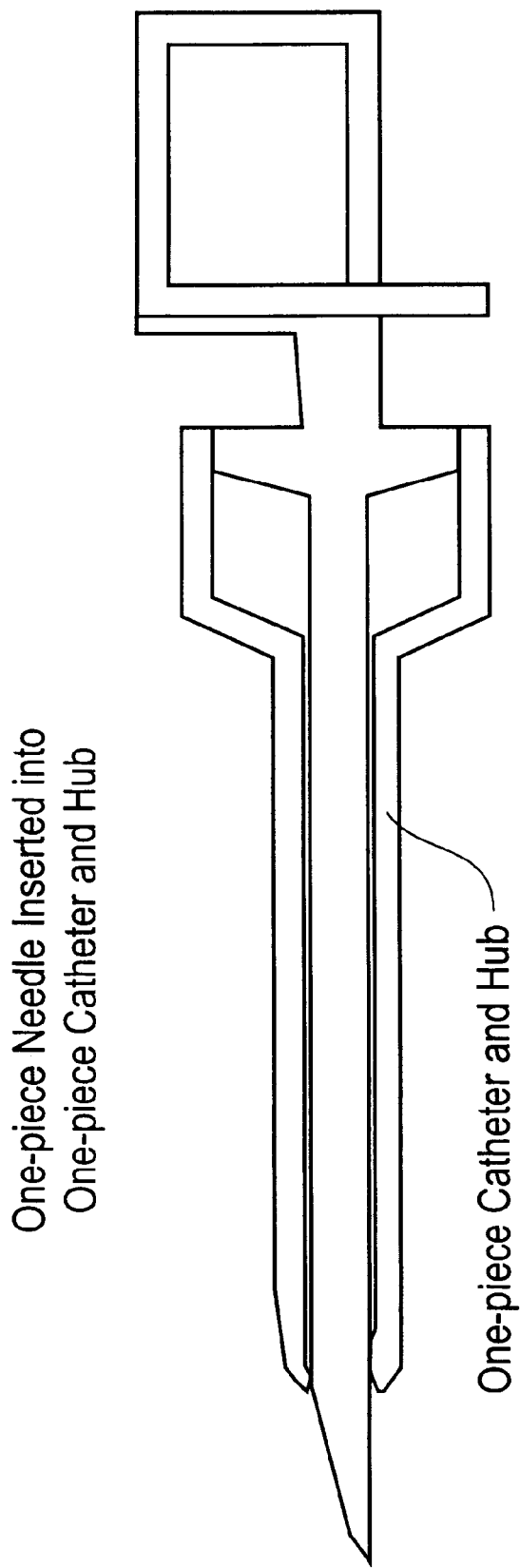
FIG. 19 illustrates the one-piece needle of FIG. 18 inserted into a catheter and hub in accordance with one embodiment of the invention.

FIG. 19 illustrates the one-piece needle formed from the process illustrated in FIGS. 1–5 locked in place by using a catheter and hub that has a recessed region for receiving portion 440 of the one-piece needle.

Figure 20:
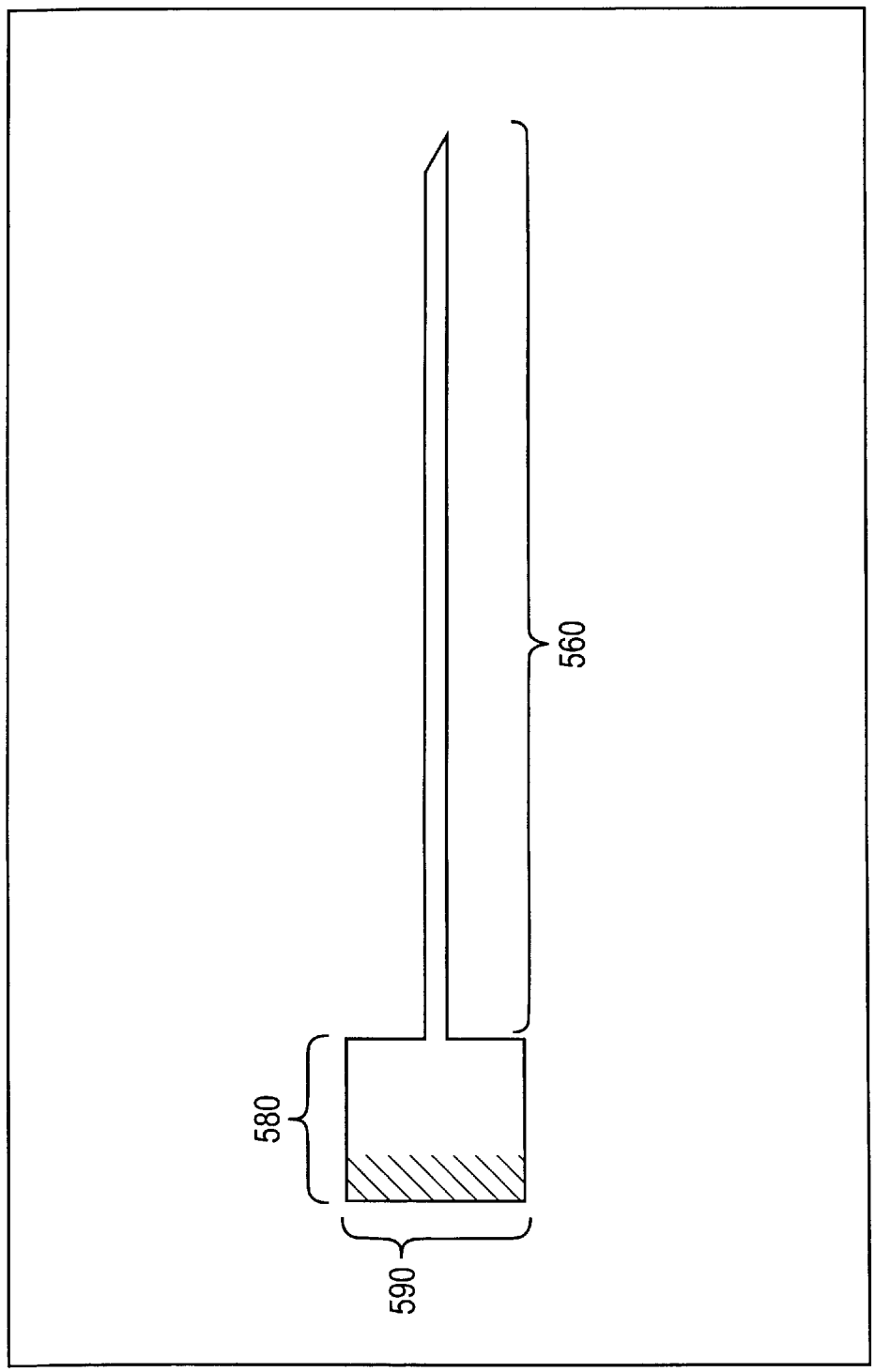
FIG. 20 illustrates a one-piece needle having a substantially cylindrical or substantially square head in accordance with one embodiment of the invention.
Figure 21:
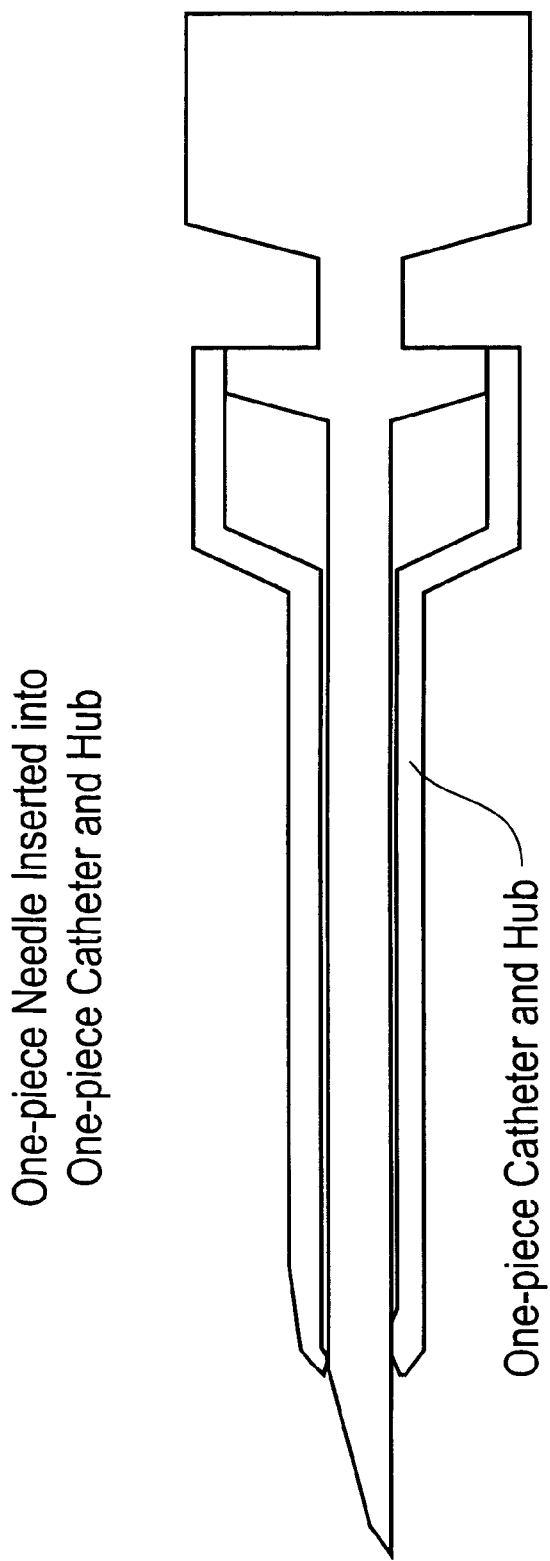
FIG. 21 illustrates the one-piece needle of FIG. 20 inserted into a catheter and hub in accordance with one embodiment of the invention.

FIG. 20 illustrates a one-piece needle that comprises a substantially cylindrical or substantially square head at the proximal end formed by segments 580 and 590. Section 580 may range in length from 0.5 inches to 2.0 inches. The length and diameter of needle portion 560 depends upon the gauge of the needle used as described above. FIG. 21 illustrates the one-piece needle formed in FIGS. 1–5 inserted into a hub and catheter.

Figure 22:
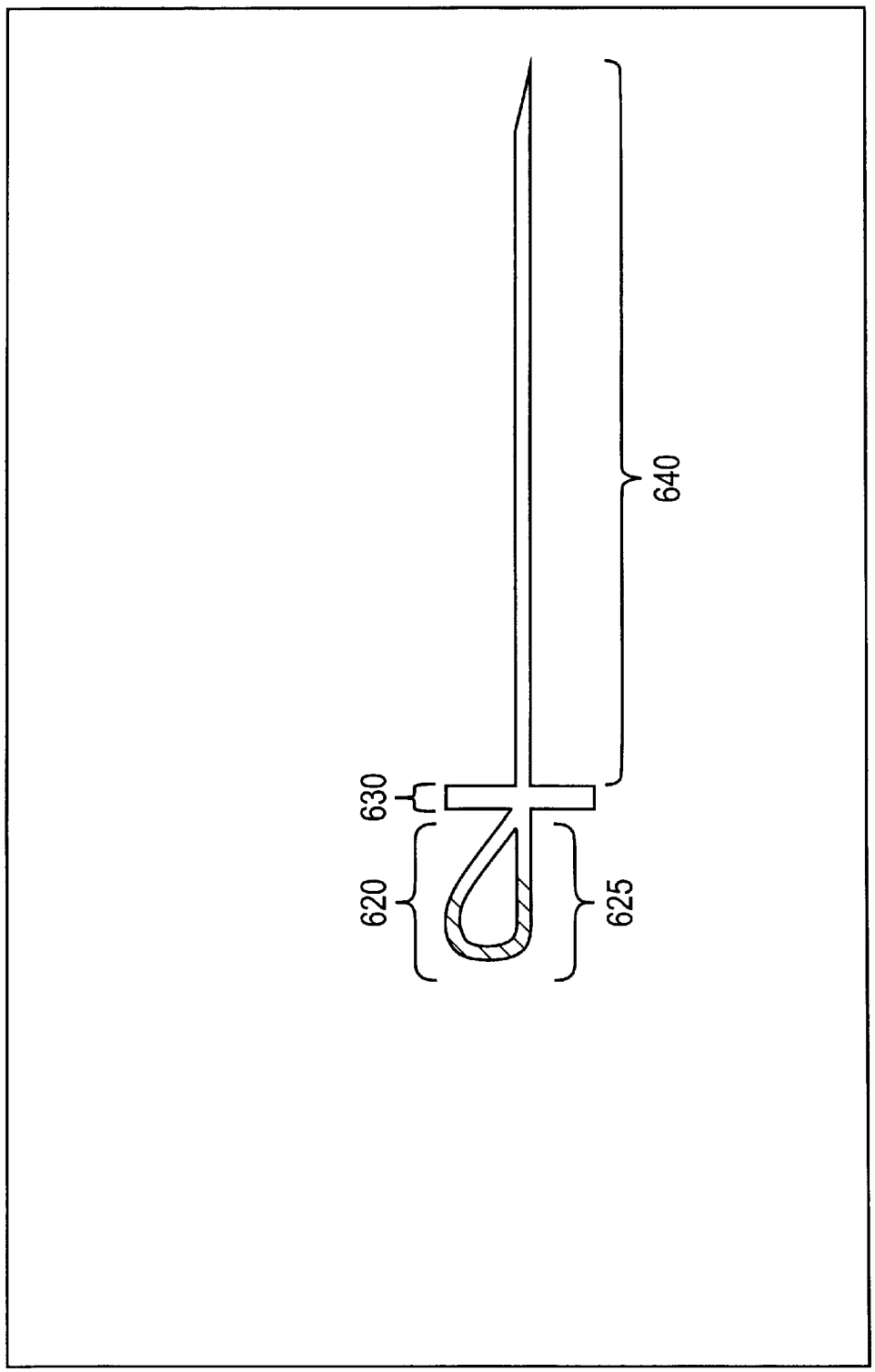
FIG. 22 illustrates a one-piece needle having a substantially looped head in accordance with one embodiment of the invention.

FIG. 22 illustrates a one-piece needle that comprises a head that has a straight portion 625 and an angled portion 620 that are joined together at disk portion 630. Needle portion 640 forms the distal portion of the one-piece needle. Straight portion 625 has a length that ranges between 0.5 to 2.0 inches. Angled portion 620 generally has a radius that ranges from approximately 0.4 to 1.0 inches.

Figure 23:
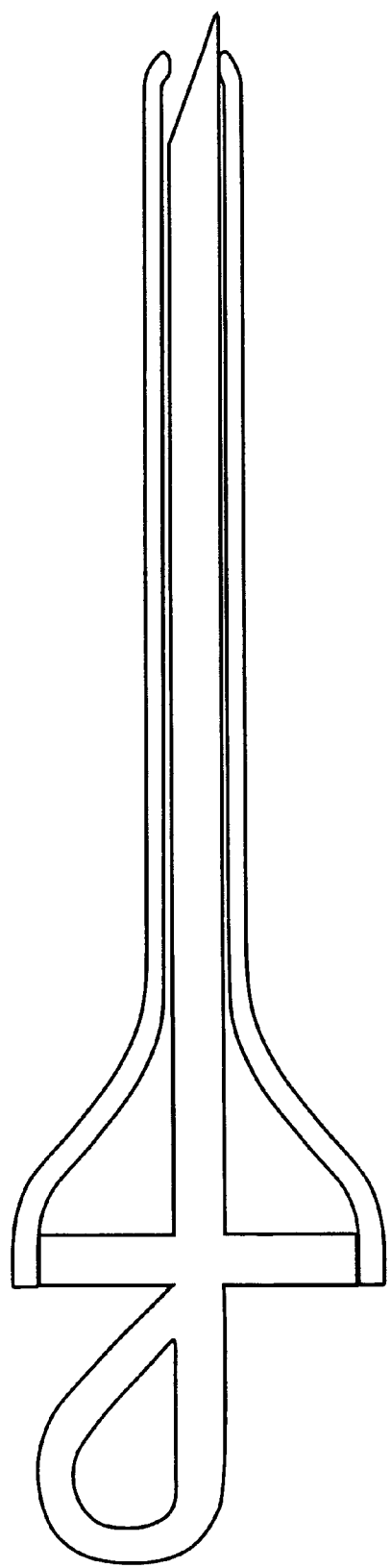
FIG. 23 illustrates a one-piece needle inserted into a catheter and hub in accordance with one embodiment of the invention.

FIG. 23 illustrates the one-piece needle formed from the process shown in FIGS. 1–5 inserted into a catheter and hub. It will be appreciated that the one-piece needle tip formed from this process is solid. Additionally, the one-piece needle may have a surface groove. The surface groove may have a variety of shapes as illustrated in FIG. 9 to 13, and 24 to 29.

Given the variety of one-piece needles that may have surface grooves, FIGS. 24 through 29 illustrate a variety of surface grooves in the one-piece needles formed by using techniques described herein.

Figure 24:
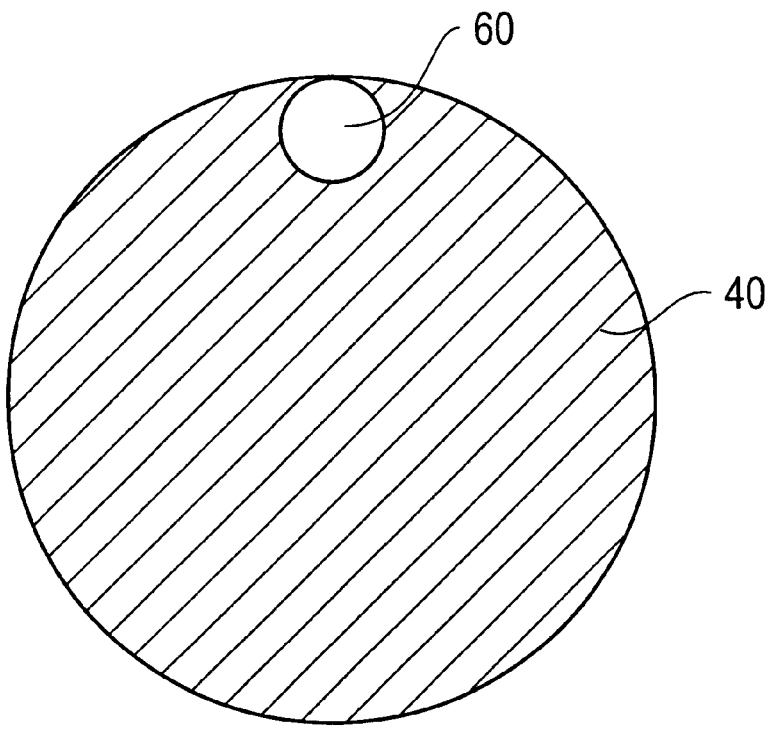
FIG. 24 illustrates a cross-section of a solid tip needle with a surface groove in accordance with one embodiment of the invention.

FIG. 24 illustrates a cross-section of a solid tip needle with a surface groove in accordance with an embodiment of the invention. Surface groove 60 is substantially circular in shape and is located in the wall of needle 40 near the outer diameter of needle 40. The surface groove has a depth that ranges from 0.001 inches to 0.05 inches depending upon the needle gauge. It will be appreciated that surface groove 60 generally extends the length of needle 40 or any portion thereof.

Figure 25:
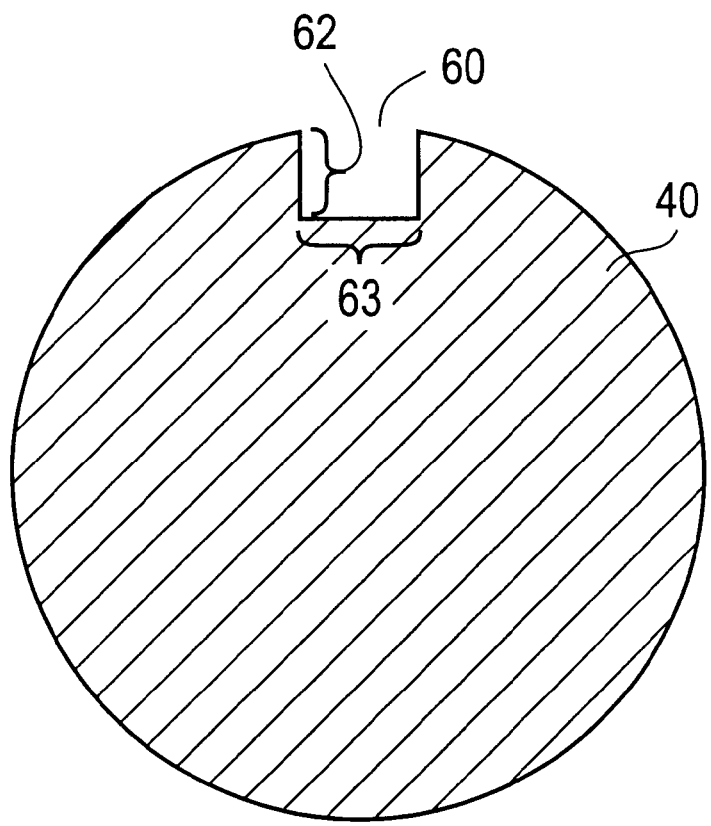
FIG. 25 illustrates a cross-section of a solid tip needle with a rectangular shaped surface groove in accordance with one embodiment of the invention.

In yet another embodiment of the invention, FIG. 25 illustrates a cross-section of a solid tip needle with a substantially rectangular portion shaped surface groove with one side that is open. Surface groove 62 ranges from 0.001 inches to 0.05 inches and the width 63 ranges from 0.001 inches to 0.05 inches both depending upon the needle gauge. Surface groove 60 allows blood to enter at the distal end of surface groove 60.

Figure 26:
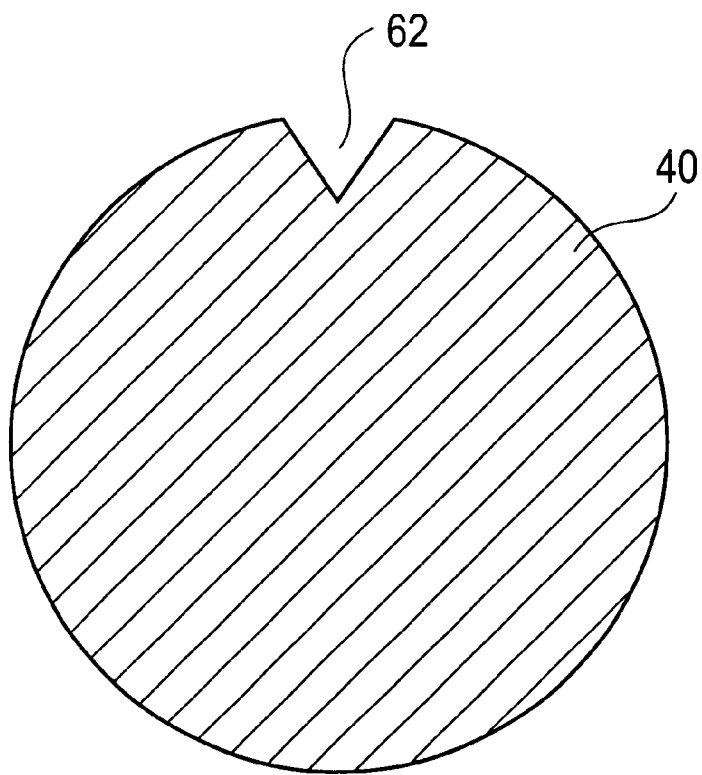
FIG. 26 illustrates a cross-section of a solid tip needle with a v-shape surface groove in accordance with one embodiment of the invention.

FIG. 26 illustrates a cross-section of a solid tip needle with a surface groove having a substantially v-shape in accordance with an embodiment of the invention. Each side that makes up the v-shape ranges from 0.001 inches to 0.05 inches depending upon the needle gauge. With this shape of a surface groove, blood flow will have an increased rate of speed at the outer ends of the v-shaped surface groove and a slower rate of movement at the central end of v-shaped surface groove.

Figure 27:
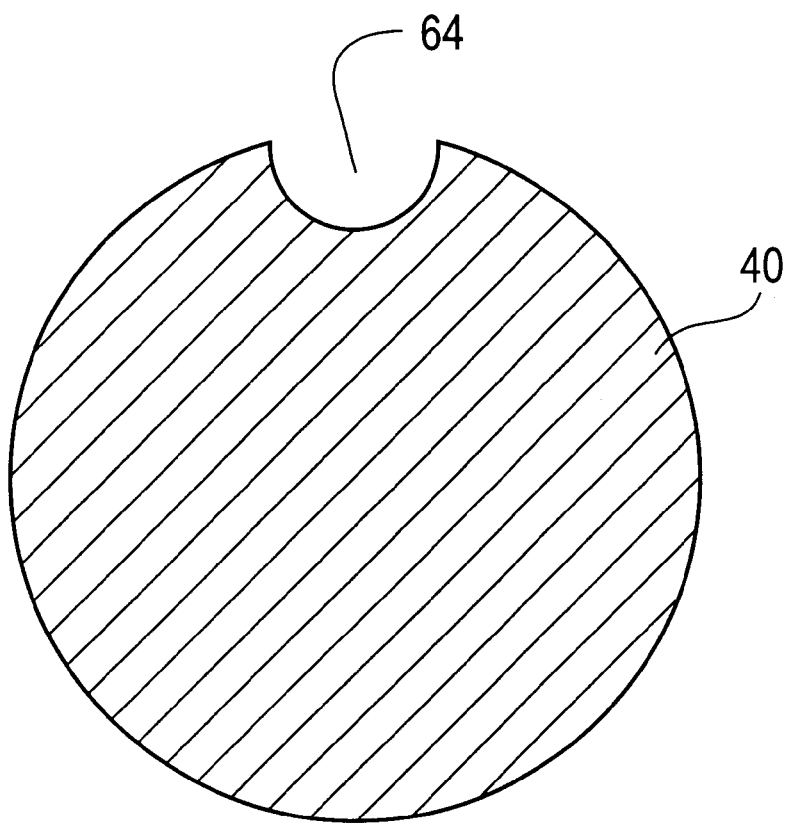
FIG. 27 illustrates a cross-section of a solid tip needle with a surface groove having a half circle shape in accordance with one embodiment of the invention.

FIG. 27 illustrates a cross section of a solid tip needle with one surface groove 64 having a substantially half-circle shape in accordance with an embodiment of the invention. The surface groove has the depth approximately in the range of 0.001 inches to 0.05 inches depending upon the needle gauge. Surface groove 64 is formed at the outer surface of needle 40. Surface groove 64 may extend the length of needle 40 or any portion thereof. Because needle 40 is solid, blood flows around the side of needle 40 into and through surface groove 64.

Figure 28:
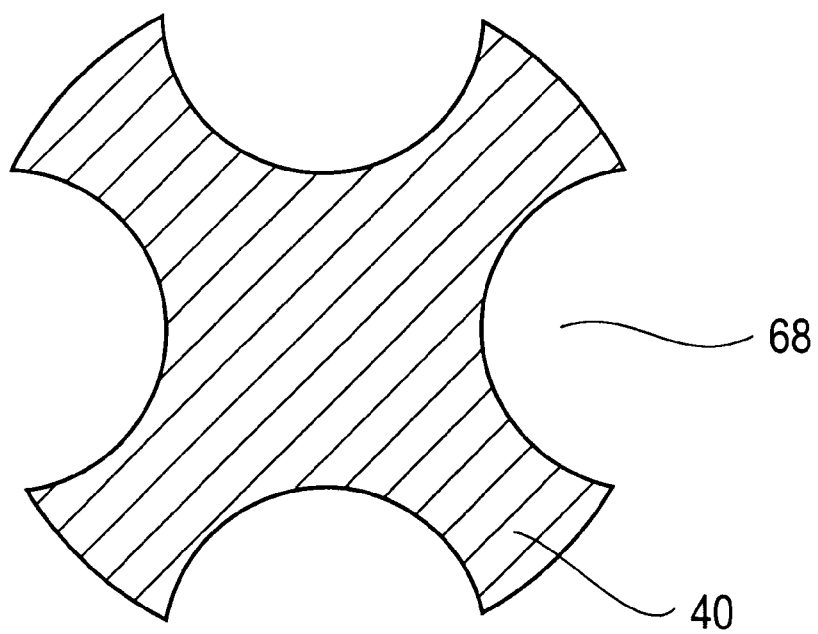
FIG. 28 illustrates a cross-section of a solid tip needle with a plurality of surface grooves having a half circle shape in accordance with one embodiment of the invention.

In yet another embodiment of the invention, FIG. 28 illustrates a plurality of substantially half-circle surface grooves 68 in solid tip needle 40. The depth of each substantially half circle ranges from 0.001 inches to 0.05 inches depending upon the needle gauge. Blood or other bodily fluids flow through surface groove 68.

Figure 29:
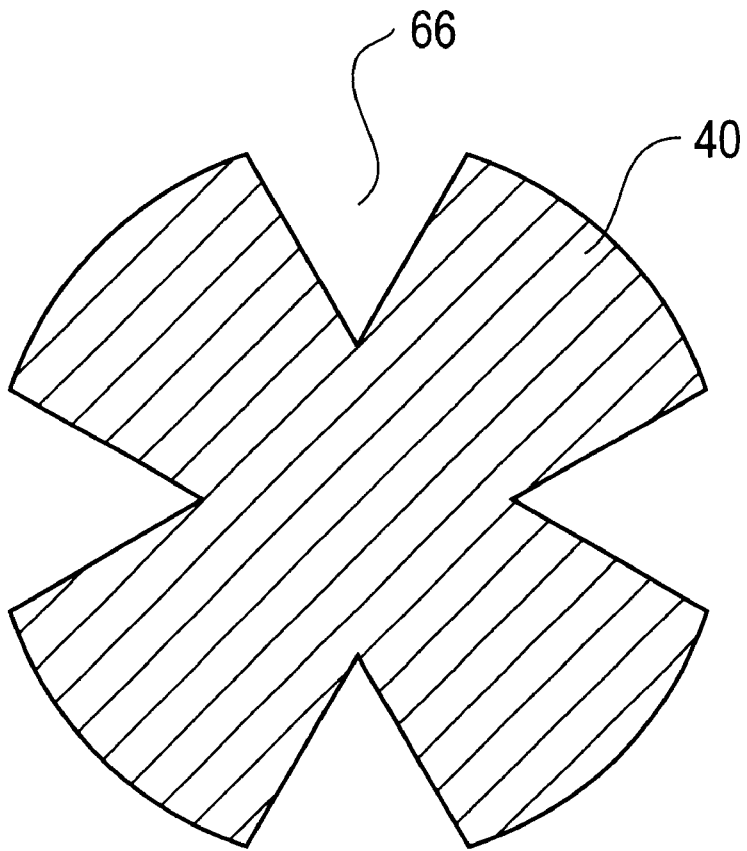
FIG. 29 illustrates a cross-section of a solid tip needle with a plurality of surface grooves having a substantially v-shape in accordance with one embodiment of the invention.

FIG. 29 illustrates a plurality of substantially v-shaped surface grooves 66 in accordance with an embodiment of the invention. Each surface groove may extend the entire length of needle 40 or any portion thereof. As noted previously, the flow of blood travels at an increased rate at the outer ends of the v-shape and flows more slowly at the central portion of the v-shape surface groove. Each side of the v-shape surface groove ranges from 0.001 inches to 0.05 inches depending upon the needle gauge.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method comprising:
   introducing photoresist onto a substrate;
   introducing a photomask onto the substrate; and
   exposing the substrate to a light thereby forming a one-piece vascular access device having at least one groove;
   wherein the at least one groove is adjacent to a distal end of the device.

2. The method of claim 1, wherein the groove has a length that ranges from about 0.5 inches to about 2.5 inches.

3. The method of claim 1, wherein the groove has a width that is about 0.001 inches to about 0.05 inches.

4. The method of claim 1, wherein the substrate has a tensile strength of at least 300,000 psi.

5. The method of claim 1, wherein a head of the vascular access one-piece device has a shape which is one of a square, a spiral, a cylinder, a sphere, a triangle, a pentagon, a hexagon, and an octagon.

6. The method of claim 1, wherein a proximal portion of the vascular access one-piece device is spiral.

7. A method comprising forming a one-piece vascular access device having at least one groove:

coating at least one side of a substrate with photoresist;

exposing the photoresist to light, wherein a plurality of vascular access one-piece needles are formed, each needle having at least one groove formed on at least one side of each needle and each needle having a pointed end;

removing the unexposed photoresist; and exposing the substrate to an etchant to remove substrate not protected by the photoresist;

wherein the at least one groove is adjacent to the pointed end of the needle.

8. The method of claim 7, wherein the groove has a length that ranges from about 0.5 inches to about 2.5 inches.

9. The method of claim 7, wherein the groove has a width that is about 0.001 inches to about 0.05 inches.

10. The method of claim 7, wherein the substrate has a tensile strength of at least 300,000 psi.

11. The method of claim 7, wherein a head of the vascular access one-piece needle has a shape which is one of a square, a spiral, a cylinder, a sphere, a triangle, a pentagon, a hexagon, and an octagon.

12. The method of claim 7, wherein a proximal portion of the vascular access one-piece needle is spiral.

13. A method comprising:

introducing a positive-acting photoresist onto a substrate;

introducing a photomask onto the substrate;

aligning the photomask; and exposing the substrate to a light thereby forming a one-piece vascular access device having at least one groove;

wherein the at least one groove is adjacent to a distal end of the device.

14. The method of claim 13, wherein the groove has a length that ranges from about 0.5 inches to about 2.5 inches.

15. The method of claim 13, wherein the groove has a width from about 0.001 inches to about 0.05 inches.

16. A method comprising:

introducing a negative-acting photo resist onto a substrate;

introducing a photomask onto the substrate;

aligning the photomask; and exposing the substrate to a light thereby forming a one-piece vascular access device having at least one groove, wherein the groove has a width that is about 0.001 inches to about 0.05 inches.

17. The method of claim 16, wherein the groove has a length that ranges from about 0.5 inches to about 2.5 inches.

* * * * *